United States Patent [19]

Depoortere et al.

[11] Patent Number: 5,064,836
[45] Date of Patent: Nov. 12, 1991

[54] IMIDAZOPYRIDINE FOR USE AS AN ANAESTHETIC

[75] Inventors: Henri Depoortere, Dampierre; Pascal George, St Arnoult en Yvelines, both of France

[73] Assignee: Synthelabo, Paris, France

[21] Appl. No.: 619,428

[22] Filed: Nov. 29, 1990

[30] Foreign Application Priority Data

Nov. 30, 1989 [FR] France ................... 89 15768

[51] Int. Cl.$^5$ ............................ A61K 31/44
[52] U.S. Cl. ................................ 514/300
[58] Field of Search ......................... 514/300

[56] References Cited
FOREIGN PATENT DOCUMENTS 0172096 2/1986 European Pat. Off. ............ 514/300

OTHER PUBLICATIONS

*Dorland's Illustrated Medical Dictionary*, 27th Edition, 1988, pp. 79 and 801.
*McGraw-Hill Dictionary of Scientific and Technical Terms*, 2nd Edition, pp. 75 and 786.

Primary Examiner—Jerome D. Goldberg
Attorney, Agent, or Firm—Wegner, Cantor, Mueller & Player

[57] ABSTRACT

A method of anaesthetizing a subject in need of anaesthetizing, which comprises administering to the subject an anaesthetically effective amount of N-[[2-(4-ethylphenyl)-3-imidazo[1,2-a]pyridinyl]methyl] N,3-dimethylbutanamide or a pharmaceutically acceptable salt thereof.

2 Claims, No Drawings

IMIDAZOPYRIDINE FOR USE AS AN ANAESTHETIC

The present invention relates to a method of anaesthetizing a subject.

N-[[2-(4-ethylphenyl)-3-imidazo[1,2-a]pyridinyl]methyl]N,3-dimethylbutanamide of formula

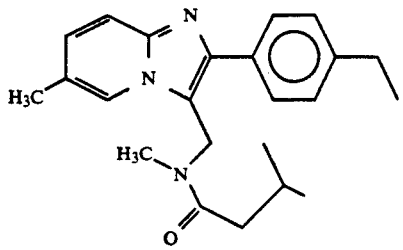

and pharmaceutically acceptable acid addition salt thereof have been described in European Patent No. 0,172,096.

A preparation of the compound and of its methanesulfonate is described below and illustrated in the reaction scheme.

1. Preparation of N-[[2-(4-ethylphenyl)-3-imidazo[I,2-a]pyridinyl]methyl]N,3-dimethylbutanamide.

1.1. 2-Bromo-1-(4-ethylphenyl)-1-ethanone. 43.7 g (14 ml) (0.27 mol) of bromine are added dropwise to a solution of 40 g (40 ml) (0.27 mol) of 1-(4-ethylphenyl)-1-ethanone in 250 ml of CH2C12. When finished, the mixture is stirred for ½ h and is then washed several times with water. The organic phase is separated off, dried over MgSO4, filtered, and the solvent is evaporated off; 60 g of a dark oil are obtained. The product is employed in this form for the next stage.

1.2. 6-Methyl-2-(4-ethylphenyl)imidazo[1,2-a]pyridine. Into a 1 liter conical are introduced, in succession: 60 g (0.2 mol) of 2-bromo-1-(4-ethylphenyl)-1-ethanone prepared in the preceding stage (77% purity), 21.7 g (0.2 mol) of 2-amino-5-methylpyridine, 34 g (0.4 mol) of NaHCO3 and 540 ml of 95% ethanol. The mixture is refluxed for 1 h 30 min and the solvent is then evaporated off. The residue is taken up with CH2Cl2 and is washed with water. The organic phase is separated off, dried over Na2SO4, filtered, and the solvent is evaporated off. The residue is taken up with ether; a solid is obtained, which is dried under vacuum. Yield: 46 g, that is 100%. Mp =146°-147° C.

1.3. 6-Methyl-2-(4-ethylphenyl)-3-imidazo[1,2-a]pyridinemethanol. 15 g (0.0634 mol) of the preceding imidazopyridine and 47.6 g (44 ml) (0.587 mol) of formaldehyde at a concentration of 37% in water are introduced into 225 l of glacial acetic acid. The solution is heated to 50° C. and stirred for 3 h. The acid and the water are then evaporated off. The residue is taken up in water and aqueous ammonia to pH ≧9 and with CH2Cl2. The insoluble material between the two phases is collected by filtration and dried. Yield: 7.37 g, that is 43%. Mp =215°-216° C.

1.4. N-[[2-(4-ethylphenyl)-3-imidazo[1,2-a]pyridinyl]methyl]-3-methylbutanamide. 2.4 g (0.009 mol) of 3-imidazo[1,2-a]pyridinemethanol and 24 ml of isovaleronitrile are introduced into a round bottom flask. The mixture is stirred. 4.64 g (2.52 ml) (0.0453 mol) of sulfuric acid are added to it dropwise. The mixture is heated until an oil separates. The supernatant liquid is employed for a second fraction. The oil (the heel) is hydrolysed with ice and then treated with aqueous ammonia. The amide is extracted with CH2C12, the solvent is evaporated off and the residue is washed with pentane and then dried. Yield: 8.4 g, that is 89%. Mp =154°-155° C.

1.5. N-[[2-(4-ethylphenyl)-3-imidazo[1,2a)pyridinyl]methyl]N,3-dimethylbutanamide. 1.28 g (0.0268 mol) of NaH at a concentration of 50% in oil are introduced into a 250-ml round bottom flask and the mixture is washed with pentane. 33 ml of THF and 1.7 ml of DMF are then added and purged with argon. 4.68 g (0.134 mol) of secondary amide dissolved in 55 ml of THF and 2.7 ml of DMF containing 1.7 ml (0.268 mol) of CH3I are added. The mixture is stirred at room temperature for 1 h. At the end of reaction the excess NaH is destroyed with a little methanol and the solvent is evaporated off. The residue is taken up with CH2Cl2 and the organic phase is washed and separated off and then dried over Na2SO4. After filtration the solvent is evaporated off. The residue is purified by flash chromatography. (97 CH2Cl2–3 CH3OH). Yield: 3.58 g, that is 73%.

2. Preparation of N-[[2-(4-ethylphenyl)-3-imidazo[1,2-a]pyridinyl]methyl]N,3-dimethylbutanamide methanesulfonate. The methanesulfonate is prepared from 4 g (0.0110 mol) of base and 1.05 g (0.0110 mol) of methanesulfonic acid in ethanol. The solution is evaporated to dryness and the residue is taken up in ether and then recrystallised from ethylacetate. Other salts may be prepared in a similar manner. Yield: 4.2 g (83%). Mp =136°-138° C.

It has surprisingly been found that N-[[2-(4-ethylphenyl)-3-imidazo[1,2-a]pyridinyl]methyl]N,3-dimethylbutanamide or a pharmaceutically acceptable salt thereof can be used as an anaesthetic.

The present invention therefore provides a method of anaesthetizing a subject in need of anaesthetizing, which comprises administering to the subject an anaesthetically effective amount of N-[[2-(4-ethylphenyl)3-imidazo[1,2-a]pyridinyl]methyl]N,3-dimethylbutanamide or a pharmaceutically acceptable acid addition salt thereof.

The salt is, for example, the methanesulfonate.

The anaesthetic activity of the compound in methanesulfonate form was determined by observation of the action of the compound on the ECoG of the immobilized rat (H. Depoortere et al., Neuropsychobiology (1986) 16,157–162). In the immobilized rat the product to be studied was injected intravenously in doses increasing from 0.003 mg/kg to 30 mg/kg. It induces sleep graphs starting with the dose of 0.003 mg/kg i.v.

In doses from 3 to 10 mg.kg i.v. the product induces graphs characteristic of a general anaesthetic (predominant 3Hz monomorphic wave pattern also observed after 30 mg/kg i.v. of midazolam). In a dose of 30 mg/kg i.v. the graphs exhibit an isoelectric activity interspersed with "K complex" spikes. In the rat this activity is also observed after ketamine and propofol.

The general short-term anaesthetic effect is characterized from the behavioral standpoint by the loss of sensitive reflexes (lasting approximately 15 min) after 5 mg/kg i.v., and of the turning reflex (lasting 30 to 50 min) after 5 mg/kg i.v. of compound. Anaesthesia can also be obtained by an intraperitoneal and/or intramuscular administration of the product.

The product is also endowed with an analgesic activity demonstrated in the mouse in the "writhing test"

($AD_{50}$=0.4 mg/kg i.v.) and by the hot plate test ($AD_{100}$=0.3 mg/kg i.v.).

The compound and its pharmaceutically acceptable acid addition salts can be employed as general anesthetics for the induction and/or maintenance of anaesthesia. They can also be employed in perfusions in the case of intensive care and also for surgical operations of short duration (e.g. in dentistry and endoscopies). The compound and its pharmaceutically acceptable acid addition salts can also be employed as local anesthetics, for example in the form of adrenalised 0.25 to 2% solutions.

The compound and its salts may be employed by themselves or in combination with other anesthetics (volatile or nonvolatile), muscle relaxants and/or analgesics. They may be presented in any suitable form of administration (tablets, gelatin capsules or injectable solutions). The posology may range from 0.01 to 0.3 mg/kg intravenously.

Diagram

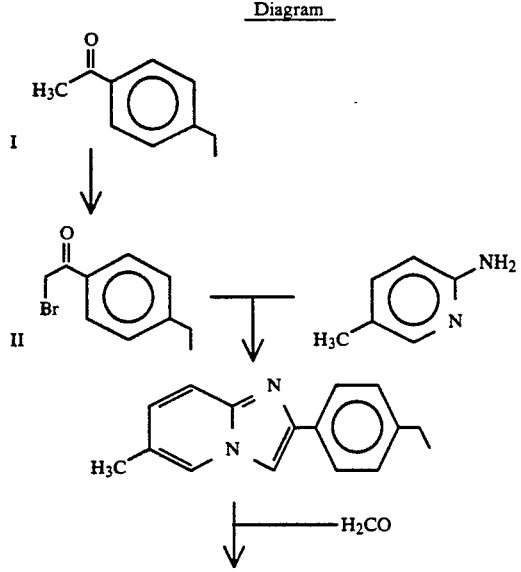

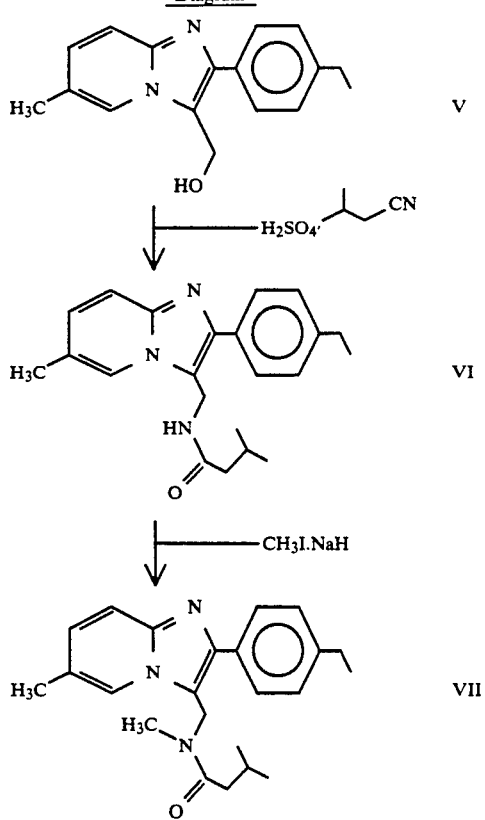

We claim:

1. A method of anaesthetizing a subject in need of anaesthetizing, which comprises administering to the subject an anaesthetically effective amount of N-[[2-(4-ethylphenyl)-3-imidazo[1,2-a]pyridinyl]methyl]N,3-dimethylbutanamide or a pharmaceutically acceptable acid addition salt thereof.

2. A method according to claim 1 wherein the salt is the methanesulfonate

* * * * *